United States Patent
Wadman et al.

(10) Patent No.: US 10,351,496 B2
(45) Date of Patent: Jul. 16, 2019

(54) PROCESS FOR THE PRODUCTION OF 1,4-BUTANEDIOL AND TETRAHYDROFURAN FROM FURAN

(71) Applicant: SHELL OIL COMPANY, Houston, TX (US)

(72) Inventors: Sipke Hidde Wadman, Amsterdam (NL); Jean Paul Andre Marie Joseph Ghislan Lange, Amsterdam (NL)

(73) Assignee: SHELL OIL COMPANY, Houston, TX (US)

(*) Notice: Subject to any disclaimer, the term of this patent is extended or adjusted under 35 U.S.C. 154(b) by 0 days.

(21) Appl. No.: 15/767,476

(22) PCT Filed: Oct. 13, 2016

(86) PCT No.: PCT/EP2016/074574
§ 371 (c)(1),
(2) Date: Apr. 11, 2018

(87) PCT Pub. No.: WO2017/064179
PCT Pub. Date: Apr. 20, 2017

(65) Prior Publication Data
US 2018/0282248 A1 Oct. 4, 2018

(30) Foreign Application Priority Data
Oct. 15, 2015 (EP) .................................. 15189985

(51) Int. Cl.
C07D 307/00 (2006.01)
C07C 29/17 (2006.01)
C07D 307/08 (2006.01)
C07C 31/20 (2006.01)

(52) U.S. Cl.
CPC .......... *C07C 29/172* (2013.01); *C07C 31/207* (2013.01); *C07D 307/08* (2013.01); *C07C 2521/06* (2013.01); *C07C 2521/18* (2013.01); *C07C 2523/652* (2013.01); *C07C 2523/656* (2013.01)

(58) Field of Classification Search
CPC .............. C07C 29/172; C07C 2521/06; C07C 2521/18; C07C 2523/656; C07C 2523/652; C07D 307/08

USPC ........................................................ 549/429
See application file for complete search history.

(56) References Cited

U.S. PATENT DOCUMENTS 5,905,159 A 5/1999 Fischer et al.

FOREIGN PATENT DOCUMENTS

| DE | 19510438 A1 | 9/1996 |
| WO | 0222593 A1 | 3/2002 |
| WO | 2012041990 A1 | 4/2012 |

OTHER PUBLICATIONS

Grant et al, Grant& Hackh's Chemical Dictionary, 1987, 5th ed, p. 433 ( 3 pages in total). (Year: 1987).*
International Search Report and Written Opinion for PCT Patent Application No. PCT/EP2016/074574, dated Dec. 15, 2016, 8 pages.
Hoydonck et al., "Furfural and Derivatives", Ulmann's Encyclopedia of Industrial Chemistry, vol. 16, 2012, pp. 285-313.
Zeitsch, "The Chemistry and Technology of Furfural and its Many By-Products", Sugar Series 13, Elsevier, 2000, 20 pages.
Lange et al., "Furfural—A Promising Platform for Lignocellulosic Biofuels", ChemSusChem, vol. 5, Issue 1, Jan. 9, 2012, pp. 150-166.
Watson. "Butane-1,4-diol from Hydrolytic Reduction of Furan", Ind. Eng. Chem. Prod. Res. Dev., vol. 12, Issue No. 4, Dec. 1973, p. 310-311.
Pan et al., "Catalytic Conversion of Furfural into a 2,5-Furandicarboxylic Acid-Based Polyester with Total Carbon Utilisation", ChemSusChem, vol. 6, Issue No. 1, Jan. 2013, pp. 47-50.
Dunlop et al., "The Furans", Reinhold Publ. Co., ACS Monograph Series, 1953, 4 pages.

* cited by examiner

*Primary Examiner* — Taylor V Oh

(57) ABSTRACT

The present invention provides a process for the preparation of 1,4-butanediol and tetrahydrofuran said process comprising contacting furan with hydrogen and water in the presence of a supported catalytic composition comprising at least one first metal selected from those in groups 8 to 10 of the periodic table and a further metal selected from manganese, molybdenum, niobium and tungsten.

7 Claims, No Drawings

PROCESS FOR THE PRODUCTION OF 1,4-BUTANEDIOL AND TETRAHYDROFURAN FROM FURAN

PRIORITY CLAIM

The present application is the National Stage (§ 371) of International Application No. PCT/EP2016/074574, filed Oct. 13, 2016, which claims priority from European Application No. 15189985.3, filed Oct. 15, 2015 incorporated herein by reference.

FIELD OF THE INVENTION

The present invention relates to a process for the production of 1,4-butanediol and tetrahydrofuran from furan.

BACKGROUND OF THE INVENTION

Furan and its derivatives are useful precursors for industrial chemicals in the area of, for example, pharmaceuticals, herbicides and polymers. Furan may be converted into tetrahydrofuran (THF) and 1,4-butanediol (1,4-BDO). THF and 1,4-BDO are valuable chemicals used industrially as solvents and in the production of elastic fibres such as elastane/spandex, polybutyrate terephthalate and derivatives of gamma butyrolactone.

These chemicals are usually produced industrially via a number of routes from petrochemical feedstocks, obtainable from fossil fuels. One industrial route for the production of 1,4-BDO requires the reaction of acetylene with two equivalents of formaldehyde followed by hydrogenation of the resultant 1,4-butynediol to form 1,4-butanediol. In an alternative process, propylene oxide is converted to allyl alcohol. The allyl alcohol is then hydroformylated to form 4-hydroxybutyraldehyde, which may be hydrogenated to form 1,4-butanediol. Other traditional routes use butadiene, allyl acetate or succinic acid as starting materials. 1,4-butanediol may also be produced as a side-product in a method for making tetrahydrofuran (THF) by oxidizing n-butane to crude maleic anhydride followed by catalytic hydrogenation.

In recent years, increased efforts have focused on producing chemicals, including 1,4-BDO and THF, from renewable feedstocks, such as sugar-based materials.

A method for obtaining furan from non-fossil fuel based sources involves the decarbonylation of furfural. Examples of reaction processes for achieving this and the subsequent conversion of the furan into its derivatives can be found in Hoydonck, H E; Van Rhijn, W M; Van Rhijn, W; De Vos, D E; & Jacobs, P A; (2012) Furfural and Derivatives, in Ullmann's Encyclopedia of Industrial Chemistry (volume 16, pp 285-313), Wiley-VCH Verlag GmBH & Co. KGaA, Weinheim; Dunlop, A P; and Peters, F N; in The Furans Reinhold Publ. Co, 1953; K. J. Zeitsch, in "The Chemistry and Technology of Furfural and its Many By-products" Sugar Series 13, Elsevier, 2000; Lange, J-P; van der Heide, E; van Buijtenen, J; and Price, R; Furfural—A Promising Platform for Lignocellulosic Biofuels; ChemSusChem 2012, 5, 150-166 and Watson, J. M.; Ind. Eng. Chem. Prod. Res. Develop., 1973, 12(4), 310. Furfural may be obtained from hemicellulose via acid hydrolysis in the liquid phase as well as in the gas phase as described in WO 2002/22593 and WO 2012/041990.

The conversion of furan to THF and 1,4-BDO by hydrogenation in the presence of water, acetic acid and Raney nickel or oxide supported nickel catalyst is described in Watson, J M; Ind. Eng. Chem. Prod. Res. Develop., 1973, 12(4), 310.

A process for the conversion of furan into 1,4-BDO and THF is taught in U.S. Pat. No. 5,905,159. This document teaches a process in which furan is converted as a reaction mixture with water and in the presence of hydrogen but in the absence of a water-soluble acid in a single stage over a hydrogenation catalyst. The hydrogenation catalyst of U.S. Pat. No. 5,905,159 contains at least one element of subgroup I, V, VI, VII or VIII in the form of a compound or in elemental form, with the restriction that the catalyst does not contain nickel alone being applicable. The preferred catalyst in this process is Re/Ru on active carbon. A similar catalyst is used in the process described in Pan, T; Deng, J; Xu, Q; Zuo, Y; Guo, Q-X and Fu, Y; Catalytic Conversion of Furfural into a 2,5-Furandicarboxylic Acid-based Polyester with Total Carbon Utilisation; ChemSusChem 2013, 6, 47-50.

Known methods in the art provide a mixture of THF, 1,4-BDO and n-butanol. Such methods generally provide THF when using a catalyst without rhenium as a promoter. The use of Re as a promoter can increase the selectivity to 1,4-BDO. However, rhenium is a rare and expensive metal.

It would be advantageous to provide a method for the production of 1,4-butanediol and tetrahydrofuran from furan in which the amount of 1,4-BDO is maximised, without using rhenium as a promoting metal on the catalyst.

SUMMARY OF THE INVENTION

Accordingly, the present invention provides a process for the preparation of 1,4-butanediol and tetrahydrofuran said process comprising contacting furan with hydrogen and water in the presence of a supported catalytic composition comprising at least one first metal selected from those in groups 8 to 10 of the periodic table and a further metal selected from manganese, molybdenum, niobium and tungsten.

DETAILED DESCRIPTION OF THE INVENTION

The present inventors have found that manganese, molybdenum, niobium and tungsten may successfully be used as promoting metals, alongside at least one first metal selected from those in groups 8 to 10 of the periodic table, in a catalyst for the conversion of furan to 1,4-butanediol and tetrahydrofuran. Such a catalyst allows an improved ratio of 1,4-BDO:THF, without the use of rhenium.

The metals may be present on the catalyst in their elemental form or as compounds.

The method of application of the metals to the support is not critical and may be effected in a wide range of ways. The metals may be applied to the support using the same or different methods and either sequentially of simultaneously. Preferably, it is more efficient to apply the two metals using the same method. Suitable methods include, for example, impregnation of the support with solutions or suspensions of the salts, complexes, hydroxides, oxides or other organic or inorganic compounds of the relevant elements, drying and optional calcination. Another possibility for applying the metals to the support is to impregnate the latter with a solution of thermally readily decomposable complexes, for example with carbonyl or hydride complexes of the metals, and to heat the carrier thus impregnated to, for example, 150 to 600° C. for thermal decomposition of the absorbed metal compounds. The metals may furthermore be deposited on the catalyst carrier by vapour deposition or by flame spraying. Subsequent reduction of the metal compound to the relevant metals or compounds of lower oxidation states by means of a reducing agent may be carried out after any method of deposition.

The first metal is selected from at least one of those in groups 8 to 10 of the periodic table. Preferably, the first metal is selected from one or more of ruthenium, palladium and platinum.

Preferably, the first metal or metals are present on the catalyst in an amount of no more than 3 wt %, more preferably no more than 1 wt %, even more preferably no more than 0.3 wt %, most preferably no more than 0.1 wt %. Suitably, the first metal or metals are present on the catalyst in an amount of at least 0.001 wt %, preferably at least 0.003 wt %, more preferably at least 0.01 wt %.

Preferably, the further metal selected from manganese, molybdenum, niobium and tungsten is present on the catalyst in an amount of at least 0.5 wt %, more preferably at least 1 wt %, most preferably at least 3 wt %. Suitably, the further metal is present on the catalyst in an amount of at most 20 wt %.

The total amount of the metals (considered as their elements and on the basis of the total weight of the catalyst), i.e. the combination of the amount of the first metal(s) and the further metal, on the catalyst may vary within wide ranges. Preferably, the total amount of said metal or metals is at least 0.01 wt %, more preferably at least 0.03 wt %, more preferably at least 0.1 wt %, more preferably at least 0.3 wt %, more preferably at least 1.0 wt %, most preferably at least 3.0 wt %. Further, preferably, the total amount of said metal or metals is at most 20 wt %, more preferably at most 15 wt %, most preferably at most 10 wt %.

Suitable supports in the present invention include oxides of aluminium, titanium, zirconium, silicon, as such or in combination with other oxides. The support can be amorphous or crystalline, including clays such as montmorillonite or zeolites, such as ZSM-5 or ZSM-10 zeolites. In another embodiment, the support is composed of carbon such as active carbon. Mixtures of different supports can, of course, also serve as supports for the catalysts to be used in the process of the invention. Preferred supports are aluminas, titanium dioxides, zirconium dioxide and active carbon. More preferred are titanium dioxide and active carbon. Most preferably, the support is active carbon.

The furan may be contacted with hydrogen either in the gas or the liquid phase.

Suitable conditions for the production of 1,4-BDO and THF from furan include gas- or liquid phase conditions in the absence or presence of gas or liquid diluent. For liquid phase condition, an inert non-polar or moderately polar solvent, such as a hydrocarbon or oxygenate, can be used. However, such a process will mainly form THF. In order for 1,4-BDO to be produced, water must be present in the reaction mixture. Further conditions include a temperature in the range of from 25 to 250° C., a pressure of from 0.1 to 10 MPa and a $H_2$:furan molar ratio in the range of from 0.2:1 to 100:1, preferably in the range of from 0.2:1 to 10:1 and most preferably in the range from 1:1 to 3:1.

Alternative suitable conditions for the production of a mixture of BDO and THF include co-feeding water as a gas or liquid at a water:furan molar ratio in the range of from 0.2:1 to 100:1, preferably in the range of 1:1 to 20:1 and most preferably 3:1 to 10:1. In this embodiment, further suitable conditions include the use of a solvent comprising water and/or oxygenates, preferably the reaction product (THF) or eventually by-products, a temperature in the range of from 100 to 350° C., preferably 120 to 250° C., most preferably 150-200° C., a pressure of from 0.1 to 15 MPa, preferably 1-10 MPa and most preferably 3-7 MPa and a $H_2$:furan molar ratio in the range of from 0.2:1 to 100:1, preferably in the range of from 1:1 to 10:1, most preferably 2:1 to 5:1.

The invention will now be illustrated by the following non-limiting examples.

EXAMPLES 1 TO 10 AND COMPARATIVE EXAMPLES 11 & 12

A number of catalysts were evaluated in a 16-reactor testing unit that can operate at up to 80 bar and 500° C. The testing unit can be fed with up to 5 gases (hydrogen, CO, $N_2$, argon and air) and two liquids. The unit allowed for on-line GC analysis of gases and semi-automated off-line GC analysis of the liquid product. Gas and liquid product yields were determined in reference to a gas standard (He) and a liquid standard (diethylene-glycol diethyl ether) that were fed together with the gas and liquid feed and were selectively collected in the gas and liquid samples, respectively.

The reactor consisted of SS316 tubes of 4.6 mm ID and 35.5 cm long, of which the central 10 cm length is isothermal. The reactor tubes were loaded with about 1 mL of catalyst, centered in the middle of the reactor while the remaining upper and lower void was filled with inert material such as SiC particles and/or porous SS316 cyclinders.

The catalysts were prepared by incipient wetness impregnation of the support with solutions of the following salts: $Ru(NO_3)_3NO$, $HReO_4$, ammonium paratungstate, ammonium hepta molybdate tetrahydrate, manganese (II) nitrate tetrahydrate and ammonium niobium oxalate.

The solutions were prepared with the concentration required to achieve the targeted metal loading. The catalysts were dried at 120° C. for 2 h in air and for half an hour at 225° C. temperature.

The catalysts supports consisted 30-80 mesh powders of monoclinic zirconia, anatase-rich titania (P25 from Degussa) and active carbon (RX-3 from Norit). Their properties are the following:

TABLE 1

| support properties | | |
|---|---|---|
| | BET m2/g | Pore volume ml/g |
| m-ZrO2 | 51.6 | 0.25 |
| TiO2 (P25) | 41.9 | 0.26 |
| C (RX-3) | 1190 | 0.81 |

The catalysts were dried and reduced for 1 h at 75° C., 4 h 120° C. and more than 4 h at 275° C. under a 30% $H_2$/70% $N_2$ flow of GHSV=625 NL/L/h at nearly atmospheric pressure. Subsequently, the temperature was lowered to 120° C., the pressure was raised to 50 atmosphere and the gas flow set to about GHSV=280 Nl/L/h and 100% $H_2$ to be ready for start-up.

The gas feed consisted of a mixture of 10% He and 90% $H_2$ and was fed at a rate of about 280 Nl per liter catalyst bed per hour. The liquid feed consisted of a mixture of 24 w % furan, 21 w % water, 50 w % ethanol and 4 w % standard. The liquid feed was introduced at a rate of about 0.8 liter per liter catalyst bed per hour. The run was carried out at a pressure of 50 bars. The temperature was ramped from 140 to 200° C. by steps of 20° C. and back to 160° C. (if indicated in Table 2). The run lasted for 200-250 hours in total.

The average yields measured at the given temperature are reported in table 2. The yields are expressed as fraction of the carbon of furan that is converted into the desired concerned. The yield may occasionally add up to slightly more than 100 C % as results of experimental inaccuracies.

TABLE 2

|   | support | M1 wt % | M2 wt % | Temp ° C. | THF Yield C % | BDO Yield C % | NBA Yield C % | BDO/THF mol/mol |
|---|---------|---------|---------|-----------|---------------|---------------|---------------|-----------------|
| 1 | $TiO_2$ | Ru 1.0  | Mo 5.0  | 160       | 12            | 7             | 6             | 0.58            |
| 2 | $ZrO_2$ | Ru 1.0  | Mo 5.0  | 200       | 24            | 10            | 10            | 0.41            |
| 3 | $TiO_2$ | Ru 0.75 | Mo 7.5  | 160       | 43            | 5             | 16            | 0.12            |
| 4 | $TiO_2$ | Ru 0.75 | Mo 7.5  | 160       | 48            | 17            | 21            | 0.35            |
| 5 | Carbon  | Ru 0.52 | Mn 1.0  | 200       | 20            | 6             | 3             | 0.30            |
| 6 | Carbon  | Ru 0.52 | Mn 5.0  | 200       | 19            | 3             | 4             | 0.16            |
| 7 | $TiO_2$ | Ru 1    | W 5     | 160       | 33            | 30            | 24            | 0.90            |
| 8 | $TiO_2$ | Ru 0.5  | Nb 2.5  | 160       | 11            | 3             | 5             | 0.27            |
| 9 | $ZrO_2$ | Ru 0.3  | Nb 1.5  | 200       | 22            | 5             | 8             | 0.22            |
| 10| $ZrO_2$ | Ru 0.3  | Nb 3.0  | 180       | 7             | 1             | 3             | 0.14            |
| 11| Carbon  | Ru 1.0  | Re 5.0  | 160       | 66            | 12            | 15.6          | 0.18            |
| 12| $TiO_2$ | Ru 0.5  | Re 5.0  | 160       | 58            | 1.3           | 22.8          | 0.02            |

As shown in this table of unoptimised examples, catalysts of the invention demonstrate good yields and selectivity to 1,4-BDO, e.g. expressed as BDO/THF molar ratio, when compared with similar catalysts in which rhenium is used as the promoting metal. This is achieved with the use of less costly and more readily available promoting metals.

That which is claimed is:

1. A process for the preparation of 1,4-butanediol and tetrahydrofuran said process comprising contacting furan with hydrogen and water in the presence of a supported catalytic composition comprising at least one first metal selected from those in groups 8 to 10 of the periodic table and a further metal selected from manganese, molybdenum, niobium and tungsten, wherein the ratio of the further metal to the first metal is greater than 5.

2. A process as claimed in claim 1, wherein the first metal is selected from one or more of ruthenium, platinum and palladium.

3. A process according to claim 1, wherein the support in the supported catalyst composition is selected from titanium dioxide, zirconium dioxide, mixtures thereof and carbon.

4. A process according to claim 1, wherein the at least one first metal is present in an amount in the range of from 0.001 to 2 wt % on the basis of the total weight of the catalyst.

5. A process according to claim 1, wherein the further metal is present in and amount in the range of from 0.5 to 20 wt % on the basis of the total weight of the catalyst.

6. A process according to claim 1, wherein the total amount of the metals (considered as their elements) on the catalyst is in the range of from 0.01 to 20 wt %.

7. A process according to claim 1, wherein the furan is contacted with hydrogen and water is co-fed at a water:furan molar ratio in the range of from 0.2:1 to 100:1, at a temperature in the range of from 100 to 350° C., a pressure of from 0.1 to 15 MPa and a $H_2$:furan molar ratio in the range of from 0.2:1 to 100:1.

* * * * *